(12) United States Patent
Seeralan et al.

(10) Patent No.: US 11,432,906 B2
(45) Date of Patent: Sep. 6, 2022

(54) DENTAL INSTRUMENT WITH A FLEXIBLE TIP END AND METHOD OF MANUFACTURE

(71) Applicant: HU-FRIEDY MFG. CO., LLC, Chicago, IL (US)

(72) Inventors: Ravi P. Seeralan, Buffalo Grove, IL (US); Alexander M. Kerstein, Chicago, IL (US); Jennifer Nemeth, Chicago, IL (US)

(73) Assignee: HU-FRIEDY MFG. CO., LLC, Chicago, IL (US)

( * ) Notice: Subject to any disclaimer, the term of this patent is extended or adjusted under 35 U.S.C. 154(b) by 261 days.

(21) Appl. No.: 16/372,084

(22) Filed: Apr. 1, 2019

(65) Prior Publication Data
US 2019/0380812 A1 Dec. 19, 2019

Related U.S. Application Data

(60) Provisional application No. 62/686,493, filed on Jun. 18, 2018.

(51) Int. Cl.
*A61C 3/00* (2006.01)

(52) U.S. Cl.
CPC ...................... *A61C 3/00* (2013.01)

(58) Field of Classification Search
CPC .. A61C 3/00; A61C 3/005; A61C 3/02; A61C 3/025; A61C 3/03; A61C 3/04; A61C 3/06; A61C 3/08; A61C 3/10; A61C 3/12; A61C 3/14; A61C 3/16; A61C 3/162; A61C 3/164; A61C 3/166; A61C 3/168; A61C 15/00; A61C 15/02; A61B 17/3213

USPC ............... 433/141, 142, 143, 146, 147, 149
See application file for complete search history.

(56) References Cited

U.S. PATENT DOCUMENTS

| 281,110 | A | | 7/1883 | Mitchell |
|---|---|---|---|---|
| 368,457 | A | | 8/1887 | Clark |
| 815,153 | A | | 3/1906 | Fritz |
| 1,253,379 | A | | 1/1918 | Hobbs et al. |
| 1,310,014 | A | | 7/1919 | O'Halloran |
| 1,410,296 | A | * | 3/1922 | Hannah .................. A61C 13/12 433/144 |

(Continued)

FOREIGN PATENT DOCUMENTS

| CA | 2344681 A1 * | 5/2000 | .......... F16B 19/1054 |
|---|---|---|---|
| GB | 268921 A | 4/1927 | |

(Continued)

OTHER PUBLICATIONS

European Patent Application No. 19167900.0, Communication Pursuant to Article 94(3) EPC, dated Sep. 28, 2020.

(Continued)

*Primary Examiner* — Nicholas D Lucchesi
(74) *Attorney, Agent, or Firm* — Marshall, Gerstein & Borun LLP (57) ABSTRACT

Dental instruments, assemblies, and components for a dental instrument are described with a two-piece tip that includes a flexible tip end and a stiff shank. Various methods of assembly are described for securing the flexible tip end to the shank including utilizing a slot in the shank and one or more pins inserted through the tip and shank, a securing material, and forming the shank with a distal portion coupled to a portion of the flexible tip end.

16 Claims, 4 Drawing Sheets

(56) References Cited

U.S. PATENT DOCUMENTS

| | | | |
|---|---|---|---|
| 1,435,902 A | 11/1922 | Derbyshire | |
| 1,505,684 A | 8/1924 | Ainsworth | |
| 1,771,182 A | 7/1930 | Lentulo | |
| 2,967,738 A | 1/1961 | Moore | |
| 3,004,362 A | 10/1961 | Day | |
| 3,023,054 A | 2/1962 | Shigekuni | |
| 3,367,335 A * | 2/1968 | Ward | A61B 17/3213 606/167 |
| 3,541,689 A | 11/1970 | Snead | |
| 3,835,641 A | 9/1974 | Goodrich | |
| 4,060,897 A * | 12/1977 | Greenstein | A61C 13/12 433/144 |
| 4,478,532 A * | 10/1984 | Puro | B25B 7/08 16/342 |
| 4,552,531 A | 11/1985 | Martin | |
| 4,738,621 A | 4/1988 | Lowder | |
| 4,743,198 A | 5/1988 | Kennedy | |
| 4,759,713 A | 7/1988 | Heiss et al. | |
| 4,809,500 A | 3/1989 | Roberts, Jr. | |
| 4,820,154 A | 4/1989 | Romhild et al. | |
| 4,854,867 A | 8/1989 | Meinershagen | |
| 5,127,833 A | 7/1992 | Kline | |
| 5,328,370 A | 7/1994 | Chen | |
| 5,342,284 A * | 8/1994 | Lemon | A46B 5/0075 15/110 |
| 5,505,617 A | 4/1996 | Skeppmark et al. | |
| 5,624,259 A | 4/1997 | Heath et al. | |
| 5,682,665 A | 11/1997 | Svanberg | |
| 6,000,215 A | 12/1999 | Roberts, Jr. | |
| 6,241,519 B1 | 6/2001 | Sedelmayer | |
| 6,379,155 B1 * | 4/2002 | Riitano | A61C 5/42 433/102 |
| 6,386,873 B1 | 5/2002 | Blank | |
| 6,419,488 B1 | 7/2002 | McSpadden et al. | |
| 6,704,625 B2 | 3/2004 | Albero et al. | |
| 6,729,877 B2 | 5/2004 | Rahman | |
| 6,997,709 B2 * | 2/2006 | Kangasniemi | A61C 3/00 433/147 |
| 7,131,982 B1 * | 11/2006 | Karapetyan | A61B 17/3213 606/167 |
| 7,249,948 B2 | 7/2007 | Hill | |
| 7,552,582 B2 | 6/2009 | Eick et al. | |
| 7,677,296 B2 | 3/2010 | Mason | |
| 8,062,033 B2 | 11/2011 | Luebke | |
| 8,083,873 B2 | 12/2011 | Luebke | |
| 8,109,464 B2 | 2/2012 | Bhargava | |
| 8,562,341 B2 | 10/2013 | Luebke | |
| 8,801,433 B1 * | 8/2014 | Charlton | A61C 3/02 433/141 |
| 9,011,147 B2 | 4/2015 | Jacquemyns | |
| 9,328,661 B2 | 5/2016 | Ho et al. | |
| 9,681,597 B1 | 6/2017 | Henshaw | |
| 10,758,319 B2 * | 9/2020 | Buist, Sr. | A61C 5/44 |
| 2005/0130099 A1 | 6/2005 | Besek et al. | |
| 2006/0063123 A1 * | 3/2006 | Cleary | A61C 7/02 433/3 |
| 2009/0007431 A1 | 1/2009 | Fischer | |
| 2009/0029323 A1 * | 1/2009 | Nejat | A46B 7/023 433/216 |
| 2012/0000483 A1 | 1/2012 | Snedden et al. | |
| 2012/0077148 A1 * | 3/2012 | Luoto | A61C 3/06 433/143 |
| 2013/0101959 A1 * | 4/2013 | Lee | A61C 3/00 433/140 |
| 2014/0329199 A1 * | 11/2014 | Becker | A61C 5/42 433/102 |
| 2016/0051339 A1 | 2/2016 | Rouiller | |
| 2016/0221684 A1 | 8/2016 | Ho et al. | |
| 2017/0128157 A1 * | 5/2017 | Muller | A61C 3/00 |
| 2018/0030944 A1 | 2/2018 | Raad | |
| 2018/0042697 A1 * | 2/2018 | Wong | A61C 3/06 |
| 2018/0125607 A1 | 5/2018 | Zastrow | |
| 2018/0235726 A1 | 8/2018 | Zastrow | |

FOREIGN PATENT DOCUMENTS

| | | |
|---|---|---|
| JP | 2014147435 A | 8/2014 |
| JP | 2015053945 A | 3/2015 |

OTHER PUBLICATIONS

European Patent Application No. 19167900.0, Partial European Search Report, dated Aug. 7, 2019.

European Patent Application No. 19167900, Extended European Search Report, dated Nov. 6, 2019.

\* cited by examiner

FIG. 10

DENTAL INSTRUMENT WITH A FLEXIBLE TIP END AND METHOD OF MANUFACTURE

CROSS-REFERENCE TO RELATED APPLICATION

This non-provisional application claims the benefit of the filing date of U.S. Provisional Application No. 62/686,493, filed Jun. 18, 2018, the entirety of which is hereby incorporated by reference.

FIELD OF THE DISCLOSURE

The present disclosure relates generally to dental instruments and, more particularly, to dental instruments having a flexible tip end.

BACKGROUND

Dental instruments can be used to manipulate various materials which are placed, shaped, and sculpted during procedures. Point flexibility for these instruments is desirable as flexibility aids tremendously in the sculpting and shaping of the material. Commonly, instruments of these types can be manufactured from steel. Given the metallurgic properties of steel, however, manufacturing instruments from steel results in relatively rigid points. Further, if steel points are thinned and used to manipulate materials in the desired manner, the points can break over time, if not immediately, making them potentially unsafe to use.

SUMMARY

In accordance with a first aspect, a dental instrument is disclosed that includes a handle and a two-piece tip attached to the handle. The two-piece tip includes a shank including a distal portion with an end surface having a slot, where the distal portion extends along a longitudinal axis. The distal portion further has an aperture extending therethrough in a direction generally orthogonal to the longitudinal axis. The two-piece tip further includes a flexible tip end having a portion that is inserted within the slot, where the portion includes an aperture that extends therethrough. A pin is configured to be inserted through the apertures of the distal portion and the flexible tip end to secure the flexible tip end to the shank.

In accordance with one form, the shank can have a bent configuration, which in further forms can include first and second bends within a horizontal plane.

In accordance with another form, the flexible tip can be made of Nickel Titanium (NiTi) foil and/or can have a spatula configuration.

In accordance with another form, the apertures and pin can be sized relative to one another to create an interference fit and/or can have cylindrical configurations.

In accordance with another form, the apertures are first apertures, the pin is a first pin, and the dental instrument further includes a second aperture that extends through the distal portion in a direction generally orthogonal to the longitudinal axis, where the second aperture is spaced from the first aperture along a length of the distal portion. A second aperture of the flexible tip end that extends through the portion thereof is also included, where the second aperture is spaced from the first aperture along a length of the portion. The dental instrument of this form further includes a second pin that is configured to be inserted through the second apertures of the distal portion and the flexible tip end to secure the flexible tip end to the shank.

In accordance with another form, the two-piece tip is a first two piece tip with a first shank and a first flexible tip end, and handle includes opposing first and second ends, where the first two-piece tip is coupled to the first end. In this form, the dental instrument further includes a second two-piece tip that is attached to the second end of the handle. The second two-piece tip including a second shank including a distal portion with an end surface having a slot, where the distal portion extends along a second longitudinal axis, and an aperture that extends through the distal portion in a direction generally orthogonal to the second longitudinal axis. The second two-piece tip further includes a second flexible tip end having a portion inserted within the slot, the portion including an aperture extending therethrough, and a second pin that is configured to be inserted through the apertures of the distal portion and the second flexible tip end to secure the second flexible tip end to the second shank.

In accordance with a second aspect, a dental instrument is disclosed that includes a handle and a two-piece tip attached to the handle. The two-piece tip includes a steel shank with a distal portion having an end surface having a slot, where the distal portion extends along a longitudinal axis. The dental instrument further includes a NiTi foil tip end having a portion coupled to the distal portion of the shank. A material is disposed between the portion of the NiTi foil tip end and the distal portion to secure the NiTi foil tip end to the steel shank.

In accordance with one form, the material is one of a filler metal to secure the NiTi foil tip end to the steel shank with a brazing process or an adhesive.

In accordance with another form, the end surface of the distal portion can include a slot, and the portion of the NiTi foil tip end can be inserted within the slot.

In accordance with a third aspect, a method of manufacturing a dental instrument is disclosed that includes providing a handle and a two-piece tip attached to the handle. The two-piece tip includes a shank that includes a distal portion with an end surface having a slot, the distal portion extending along a longitudinal axis, and an aperture that extends through the distal portion in a direction generally orthogonal to the longitudinal axis. The method further includes inserting a portion of a flexible tip end into the slot so that an aperture extending through the portion aligns with the aperture of the distal portion and inserting a pin through the apertures of the distal portion and the flexible tip end to secure the flexible tip end to the shank.

In accordance with some forms, the method can include one or more of: forming the aperture through the distal portion in a direction generally orthogonal to the longitudinal axis, forming the aperture through the portion of the flexible tip end, or forming the slot through the end surface and into the distal portion of the shank along the longitudinal axis thereof.

In accordance with another form, the method further includes bending the distal portion of the shank to create at least one bend.

In accordance with another form, providing the two-piece tip includes providing the shank with first and second apertures spaced from one another and extending through the distal portion in a direction generally orthogonal to the longitudinal axis. Inserting the portion of the flexible tip end into the slot can include inserting a portion of the flexible tip end into the slot so that first and second apertures extending through the portion align with the first and second apertures of the distal portion, respectively. Further in this form, inserting the pin through the apertures of the distal portion and the flexible tip end includes inserting first and second pins through the first and second apertures, respectively, of the distal portion and the flexible tip end to secure the flexible tip end to the shank.

In accordance with a fourth aspect, a method of manufacturing a dental instrument is provided that includes providing a flexible tip end including a retaining portion and forming a shank with a distal portion coupled to the retaining portion of the flexible tip end to secure the flexible tip end to the shank.

In accordance with some forms, the method includes one or more of: providing a flexible tip end including an aperture extending therethrough, 3D printing the shank around the retaining portion of the flexible tip end, injection molding the shank around the retaining portion of the flexible tip end, forming a shank in a bent configuration, forming a handle with the shank at one end of the handle, and deforming the distal portion of the shank to clamp down on the retaining portion of the flexible tip end to secure the flexible tip end to the shank.

BRIEF DESCRIPTION OF THE DRAWINGS

The above needs are at least partially met through provision of the embodiments described in the following detailed description, particularly when studied in conjunction with the drawings, wherein.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION OF THE PREFERRED EMBODIMENTS

Dental instruments, assemblies, and components for a dental instrument are described herein with a flexible tip end and a stiff shank. A two-material dental instrument component achieves these beneficial results by utilizing the preferred properties of the two materials. In embodiments, the shank can be a stiff material, such as stainless steel, and the tip end can be a NiTi foil, also known as Nitinol foil. Nitinol foil advantageously provides a flexible tip that resiliently bends without breaking.

Figure 1:
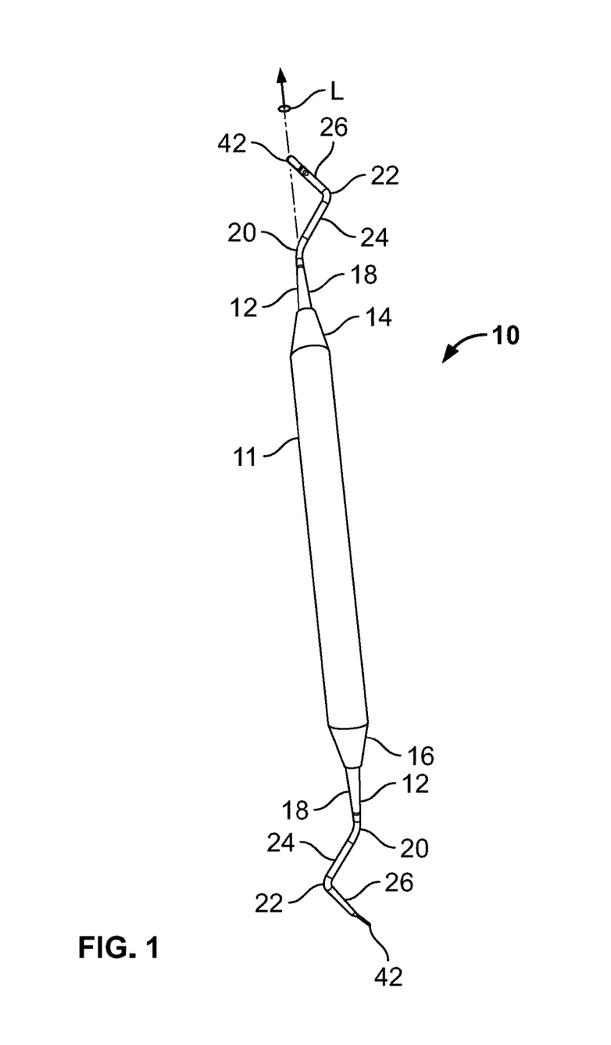
FIG. 1 is a perspective view of a dental instrument showing a handle with shanks coupled to opposite ends of the handle in accordance with various embodiments.

Example configurations and components for a dental instrument 10 are shown in FIGS. 1-10. As shown in FIG. 1, the dental instrument 10 includes a handle portion 11 having a shaft configuration for a user to grip and manipulate the dental instrument 10. The handle portion 11 has opposite first and second ends 14, 16 that can be configured to have a shank 12 coupled thereto, if desired. In the illustrated form, the first and second ends 14, 16 have a tapered configuration to provide a transition to the relatively smaller diameter of the shank 12.

Figure 2:
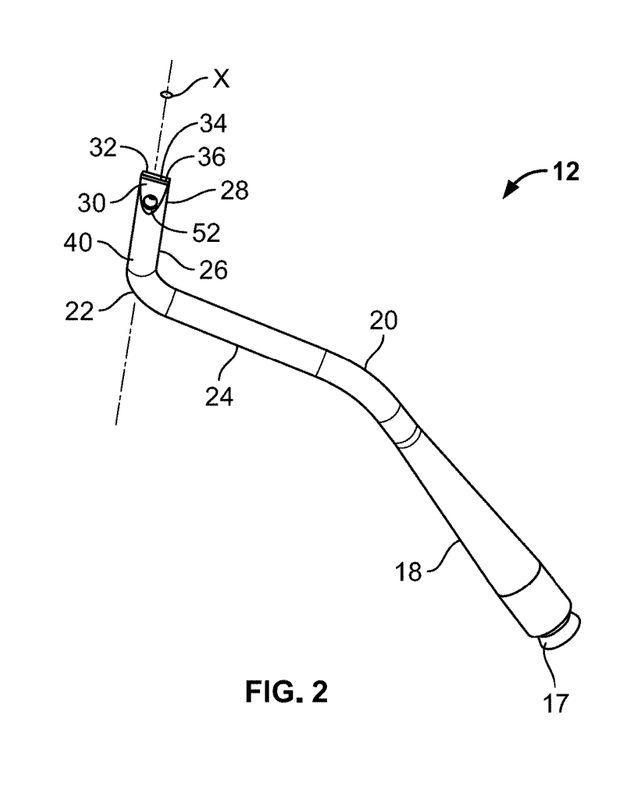
FIG. 2 is a perspective view of a shank having a bent configuration and a distal portion in accordance with various embodiments.

An example shank 12 is shown in FIG. 2 that includes a coupling end portion 17 configured to engage one of the ends 14, 16 of the handle 11, a tapering portion 18, first and second bends 20, 22, an intermediate portion 24 extending between the first and second bends 20, 22, and a distal portion 26 extending from the second bend 22 to a distal end 28 of the shank 12. The tapering portion 18 decreases a diameter of the shank 12 from adjacent to the handle 11 to the relatively smaller diameter intermediate and distal portions 24, 26, which can have a generally constant diameter.

The first bend 20 directs the shank 12 along a horizontal plane away from a longitudinal axis L (FIG. 1) of the handle 11 and the second bend 22 directs the shank 10 along the horizontal plane back towards the longitudinal axis L of the handle 11. In the illustrated form, the second bend 22 is a generally 90 degree bend and the intermediate portion 24 has a longer longitudinal length than the distal portion 26, such that the distal end 28 of the shank 10 is spaced from the longitudinal axis L of the handle 11 along the horizontal plane. Of course, other bend and length configurations are within the scope of this disclosure.

Figure 3:
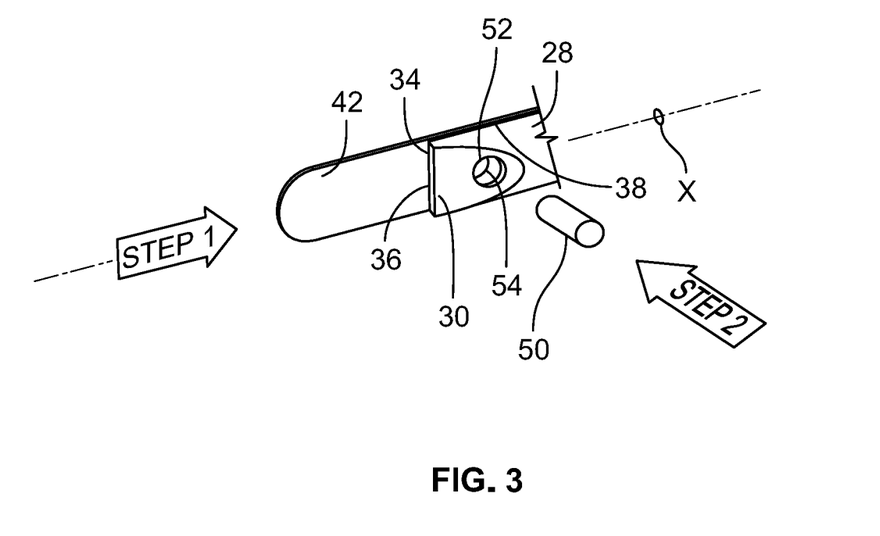
FIG. 3 is a perspective view of a portion of a distal portion of the shank of FIG. 2 with a flexible tip secured thereto and a pin in accordance with various embodiments.
Figure 4:
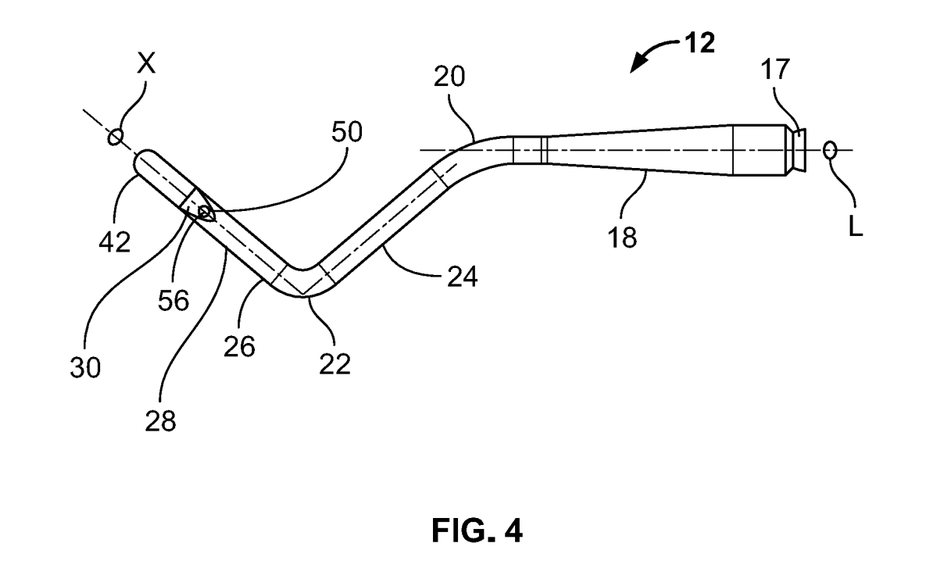
FIG. 4 is a top plan view of a shank having a flexible tip secured thereto with a pin in accordance with various embodiments.
Figure 5:
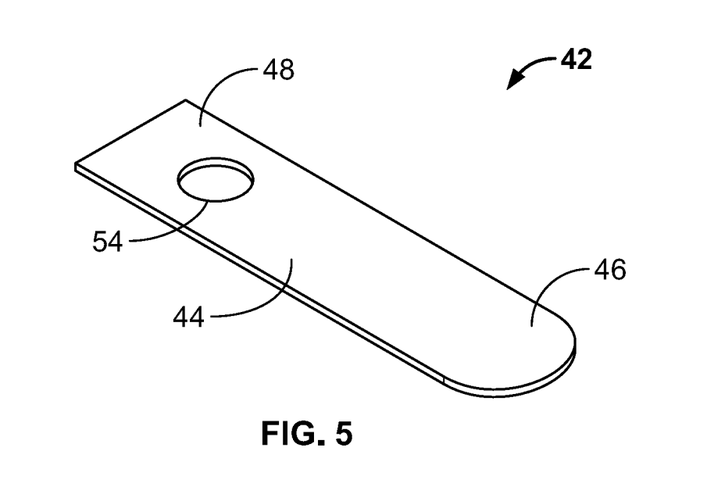
FIG. 5 is a perspective view of a flexible tip for a dental instrument with an aperture extending therethrough in accordance with various embodiments.
Figure 6:
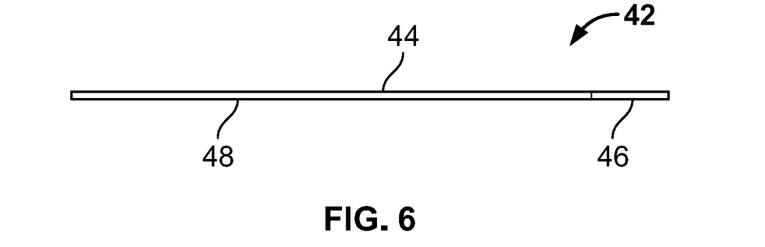
FIG. 6 is a side elevational view of the flexible tip of FIG. 5 in accordance with various embodiments.
Figure 7:
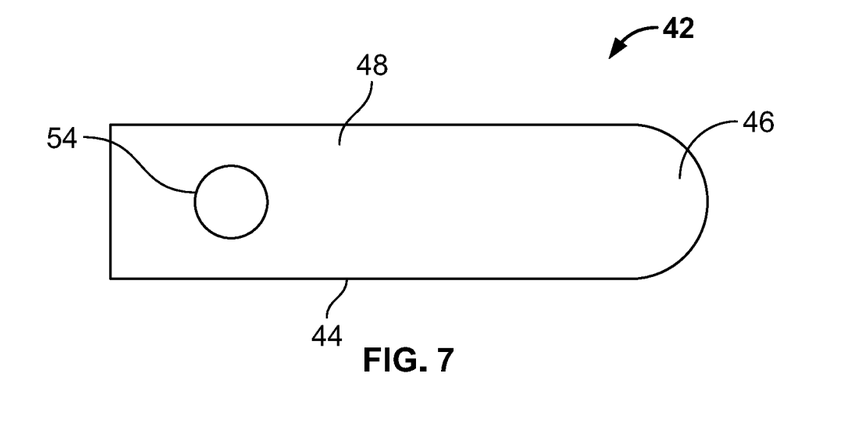
FIG. 7 is a top plan view of the flexible tip of FIG. 5 in accordance with various embodiments.

The distal end 28 of the shank 12 includes opposing planar sides 30 extending inwardly with respect to one another to a rectangular end surface 32. With the distal portion 26 being cylindrical, in the illustrated form, the planar sides 30 have a parabolic shape. A slot 34 with an opening 36 disposed along the end surface 32 extends within the distal portion 26 along a longitudinal axis X (FIG. 2) thereof to a desired depth. In the illustrated form, the slot 34 extends through the width of the distal end 28. In one example, and as depicted in FIG. 3, the slot 34 may further include openings 38 along an exterior 40 of the distal portion 26. The slot 34 can be cut into the distal end 28 of the shank 12 in a hatchet and/or hoe orientation by an electric discharge machining (EDM) wire, micro saw blade, mill, and so forth.

A tip end 42 is coupled to the distal end 28 of the shank 12 to provide desirable characteristics for a particular dental procedure. By one approach, and referring now to FIGS. 5-7, the tip end 42 is a spatula tip having a thin planar body 44 with a curved forward portion 46 and a rectangular rear portion 48. As discussed above, the shank 12 and tip end 42 are different materials and, as such, are secured together with a suitable method, examples of which are described below with reference to FIGS. 2-10. The tip end 42 also includes an aperture 54 extending through the rear portion 48 and corresponds to an aperture in the distal end 28 of the shank 12, as described more below.

In each securing example, the tip end 42 is inserted into the slot 34 to mount to the distal end 28 of the shank 12. The orientation of the planar sides 30 with respect to the horizontal plane can provide a hoe orientation for the tip end 42 or a hatchet orientation for the tip end 42, as desired. In addition, in each example, the shank 12 may comprise a stiff material, such as stainless steel, and the tip end 42 may comprise a NiTi foil, also known as Nitinol foil.

In one form, the dental instrument 10 includes shanks 12 on both sides 14, 16 of the handle 11 with one shank 12 having distal end 28 with a hoe orientation where the tip end 42 is generally orthogonal to the horizontal plane and the other shank 12 having a distal end 28 with a hatchet orientation where the tip end 42 is generally parallel with the horizontal plane to provide a user with both functionalities. Further, if desired, the tip end 42 and slot 34 can be configured so that forward portion 46 of the tip end 42 extends to intersect the longitudinal axis L of the handle 11 so that a user has precise manipulation of the tip end 42.

In a first embodiment, shown in FIGS. 2-7, the tip end 42 is secured to the distal end 28 of the shank 12 with a pin 50. More specifically, the distal end 28 of the shank 12 has an aperture 52 extending radially through a portion thereof including the slot 34 in a direction generally orthogonal to the longitudinal axis X of the distal portion 26. The aperture 54 of the tip end 42 corresponds to the aperture 52 of the distal end 28 of the shank 12. So configured, with the rear portion 48 inserted into the slot 34, the pin 50 can be inserted through both the aperture 52 and the aperture 54 to secure the tip end 42 to the shank 12. By one approach, the pin 50 can have a cross-section dimension greater than one or both of the apertures 52, 54 so that the insertion of the pin 50 therethrough creates an interference fit. Further, the pin 50 can be permanently joined to the shank 12 by swaging and grinding an outer surface 56 of the pin 50 so that the outer surface 56 is smooth and aligned with adjacent portions of the shank 12. In the illustrated form, the pin 50 and apertures 52, 54 are cylindrical. Of course, other shapes and configurations can alternatively be used. For example, the pin 50 and apertures 52, 54 can have a cross-section shape to aid in resisting rotation of the tip end 42, such as a triangle, square, star, ovular, and so forth.

Figure 8:
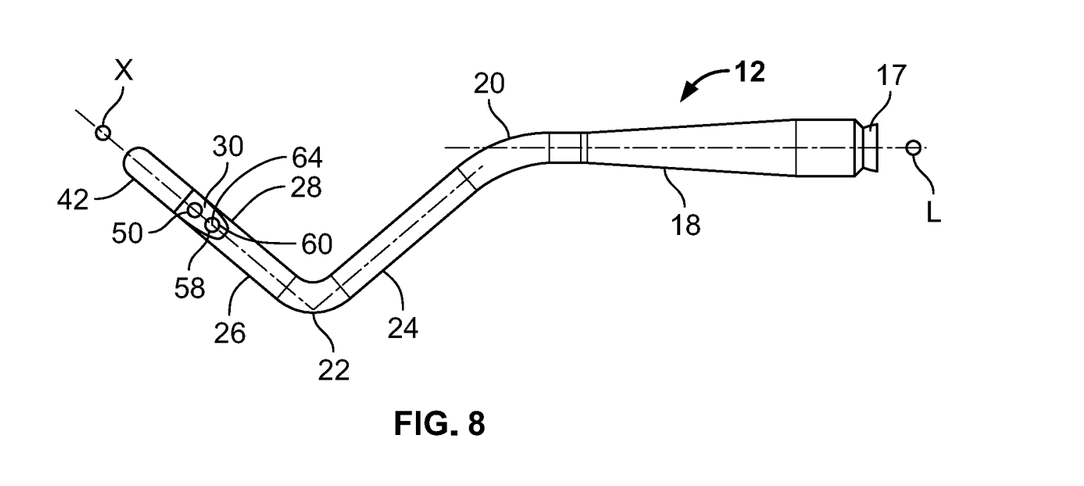
FIG. 8 is top plan view of a shank having a flexible tip secured thereto with a plurality of pins in accordance with various embodiments.
Figure 9:
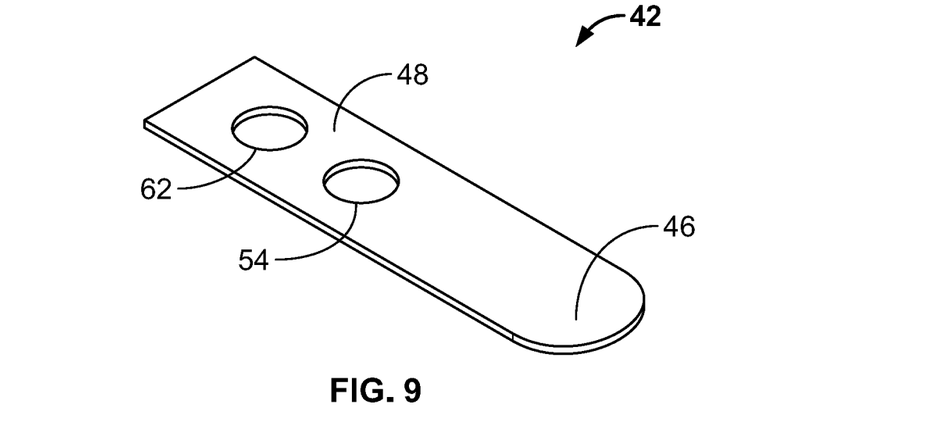
FIG. 9 is a perspective view of a flexible tip for a dental instrument with a plurality of apertures extending therethrough in accordance with various embodiments.

In a second embodiment, shown in FIGS. 8 and 9, the shank 12 has a configuration similar to the above embodiment and, as such, only the differences will be described. In this form, the tip end 42 is secured to the distal end 28 of the shank 12 with a second pin 58 in addition to the first pin 50. As such, the distal end 28 of the shank 12 has a second aperture 60 that extends radially through a portion thereof including the slot 34 in a direction generally orthogonal to the longitudinal axis X of the distal portion 26. The second aperture 60 is spaced from the first aperture 52 along a length of the distal portion 26. The tip end 42 includes a corresponding second aperture 62 that extends through the rear portion 48 thereof, as depicted in FIG. 9. So configured, with the rear portion 48 inserted into the slot 34, the second pin 56 can be inserted through the aligned second apertures 60, 62 to further secure the tip end 42 to the shank 12. Using a plurality of pins 50, 58 accommodates a larger tolerance stack when installing the tip end 42 to the shank 12, which advantageously results in more efficiencies during manufacturing. For example, the length of the tip rear portion 48 is on the shorter end of the tolerance and the depth of the shank slot 34 is on the larger end of the tolerance, a gap would exist that would allow for rotation of the tip end 42. Using two or more points to secure the tip end 42 to the shank 12 prevents tip rotation in such a tolerance scenario.

By one approach, the second pin 58 can have a cross-section dimension greater than one or both of the second apertures 60, 62 so that the insertion of the second pin 58 therethrough creates an interference fit. Further, the second pin 58 can be permanently joined to the shank 12 by swaging and grinding an outer surface 64 of the second pin 58 so that the outer surface 64 is smooth and aligned with adjacent portions of the shank 12. In the illustrated form, the second pin 58 and apertures 60, 62 are cylindrical. Of course, other shapes and configurations can alternatively be used. For example, the pins 50, 58, and apertures 52, 54, 60, 62 can have a cross-section shape to aid in resisting rotation of the tip end 42, such as a triangle, square, star, ovular, and so forth. Further, although only two pins are shown, it will be understood that additional pins can be utilized and configured in a similar manner.

In a third embodiment, the slot 34 can have a wider configuration relative to the thickness of the tip end 42 as compared to the above embodiments. This allows the tip end 42 to be inserted into the slot 34 with little to no resistance. After the tip end 42 has been inserted into the slot 34 to a desired depth, a user can then pinch the planar sides 30 of or otherwise physically deform the distal end 28 of the shank 12 to clamp down on the tip rear portion 48 to secure the tip end 42 to the shank 12. This clamping action can be achieved by the use of any suitable tools.

Figure 10:
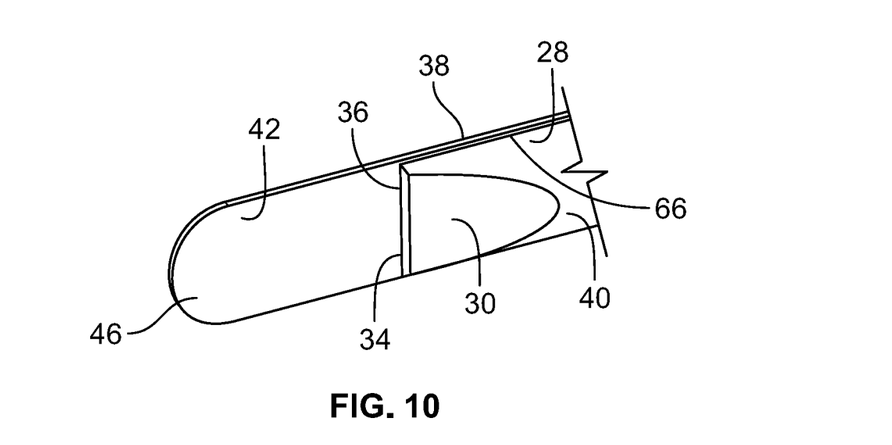
FIG. 10 is a perspective view of a portion of a distal portion of the shank of FIG. 8 with a flexible tip secured thereto with a material in accordance with various embodiments.

In other embodiments, shown in FIG. 10, the tip rear portion 48 can be inserted into the slot 34 and secured therein using a third material 66. In a first example, the third material 66 is an adhesive disposed within the slot 34 or applied to the tip rear portion 48. In a second example, the third material 66 is a filler metal flowed into the joint between the tip end 42 and shank 12 in a brazing process. Utilizing an adhesive or a brazing process secures the tip end 42 to the shank 12 without the added steps and components of the above embodiments including forming the apertures 52, 54, 60, 62 and inserting the pins 50, 58. Of course, an adhesive or brazing process can alternatively be used in combination with the pin embodiments discussed above to ensure that the tip end 42 is securely coupled to the shank 12.

A stainless steel shank provides several advantages, including: a stiffness that provides maximum control and manipulation of the tip end for a user, good material formability enabling a two-bend shank configuration that allows a user access and visibility inside a patient's mouth, no reduction in appearance or strength of the shank after being sterilized multiple times, patient bio-compatibility, and a relatively low cost manufacturing to obtain a desired shank geometry.

A Nitinol foil tip end provides several advantages, including: superelastic flexibility at room temperature, about 10-30 times ordinary metal, for spreading and controlling composite onto a tooth, implant surface, or other application location, very good strain recovery allowing for excellent kink resistance even at very aggressive bend angles, an advantageous shape memory effect allowing the foil to recover an original shape upon heating above a transformation temperature after being deformed at a lower temperature, the Nitinol foil tip can be cut into a variety of tip end shapes allowing for a range of surface access and orientations, ability to sterilize the instrument multiple times with no reduction in appearance, flexibility, or strength, and patient bio-compatibility.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

For example, the shank 12 can alternatively be composed of plastic, coated steel, or other suitable rigid material. Additionally, the shank 12 may be 3D printed into a desired shape, such as the two bend configuration described above, out of a suitable material, including steel, plastic, or other rigid material. Alternatively, the shank 12 can be injection molded into a desired shape. Further, if desired, the shank 12 can be 3D printed or injection molded around a flexible tip end 42 configured as described above. The tip end 42 can include a retaining portion, such as the apertures 54, 60 described above, or other protrusion(s) and fixed in position as the shank 12 is 3D printed or molded therearound. With the retaining portion, the tip end 42 can be fixedly secured to the shank 12. Still further, the tip end 42 may be composed of an alternate material, such as plastic, stainless steel, or a coated steel.

What is claimed is:

1. A dental instrument comprising:
   a handle;
   a two-piece tip attached to the handle, the two-piece tip including:
      a shank including a distal portion with an end surface having a slot, the distal portion extending along a longitudinal axis, and an aperture extending through the distal portion in a direction generally orthogonal to the longitudinal axis; and
      a flexible tip end comprising a Nickel Titanium foil, the flexible tip end having an elongate spatula configuration with side edges of a rectangular rear portion extending to a convex distal edge of a curved forward portion, wherein the rectangular rear portion is inserted within the slot and includes an aperture extending therethrough; and
   a pin configured to be inserted through the apertures of the distal portion and the flexible tip end to secure the flexible tip end to the shank.

2. The dental instrument of claim 1, wherein the shank has a bent configuration.

3. The dental instrument of claim 2, wherein the bent configuration comprises first and second bends within a horizontal plane.

4. The dental instrument of claim 1, wherein the shank comprises stainless steel.

5. The dental instrument of claim 1, wherein the apertures and the pin are sized relative to one another to create an interference fit.

6. The dental instrument of claim 1, wherein the apertures and the pin have cylindrical configurations.

7. The dental instrument of claim 1, wherein the apertures comprise first apertures and the pin comprises a first pin, and further comprising:
   a second aperture extending through the distal portion in a direction generally orthogonal to the longitudinal axis, the second aperture spaced from the first aperture along a length of the distal portion;
   a second aperture of the flexible tip end extending through the rectangular rear portion thereof, the second aperture spaced from the first aperture along a length of the flexible tip end; and
   a second pin configured to be inserted through the second apertures of the distal portion and the flexible tip end to secure the flexible tip end to the shank.

8. The dental instrument of claim 1, wherein the two-piece tip comprises a first two-piece tip with a first shank and a first flexible tip end, and the handle includes opposing first and second ends, the first two-piece tip coupled to the first end, the dental instrument further comprising:
   a second two-piece tip attached to the second end of the handle, the second two-piece tip including:
      a second shank including a distal portion with an end surface having a slot, the distal portion extending along a second longitudinal axis, and an aperture extending through the distal portion in a direction generally orthogonal to the longitudinal axis;
      a second flexible tip end having a portion inserted within the slot, the portion including an aperture extending therethrough; and
      a second pin configured to be inserted through the apertures of the distal portion and the second flexible tip end to secure the second flexible tip end to the second shank.

9. A method of manufacturing a dental instrument, the method comprising:
   providing a handle and a two-piece tip attached to the handle, the two-piece tip including: a shank including a distal portion with an end surface having a slot, the distal portion extending along a longitudinal axis, and an aperture extending through the distal portion in a direction generally orthogonal to the longitudinal axis;
   inserting a rectangular rear portion of a flexible tip end comprising a Nickel Titanium foil into the slot so that an aperture extending through the rectangular rear portion aligns with the aperture in the distal portion, the flexible tip end having an elongate spatula configuration with side edges of the rectangular rear portion extending to a convex distal edge of a curved forward portion; and
   inserting a pin through the apertures of the distal portion and the flexible tip end to secure the flexible tip end to the shank.

10. The method of claim 9, further comprising forming the aperture through the distal portion in a direction generally orthogonal to the longitudinal axis.

11. The method of claim 9, further comprising forming the aperture through the rectangular rear portion of the flexible tip end.

12. The method of claim 9, further comprising forming the slot through the end surface and into the distal portion of the shank along the longitudinal axis thereof.

13. The method of claim 9, further comprising bending the distal portion of the shank to create at least one bend.

14. The method of claim 9, further comprising swaging an end of the pin.

15. The method of claim 9, wherein:
providing the two-piece tip comprises providing the shank with first and second apertures spaced from one another and extending through the distal portion in a direction generally orthogonal to the longitudinal axis;
inserting the rectangular rear portion of the flexible tip end into the slot comprises inserting the rectangular rear portion of the flexible tip end into the slot so that first and second apertures extending through the rectangular rear portion align with the first and second apertures of the distal portion, respectively; and
inserting the pin through the apertures of the distal portion and the flexible tip end comprises inserting first and second pins through the first and second apertures, respectively, of the distal portion and the flexible tip end to secure the flexible tip end to the shank.

16. The method of claim 9, wherein the pin has a diameter greater than one or both of the apertures of the distal portion and the flexible tip end, such that inserting the pin through the apertures of the distal portion and the flexible tip end creates an interference fit to secure the flexible tip end to the shank.

\* \* \* \* \*